Figure 1:
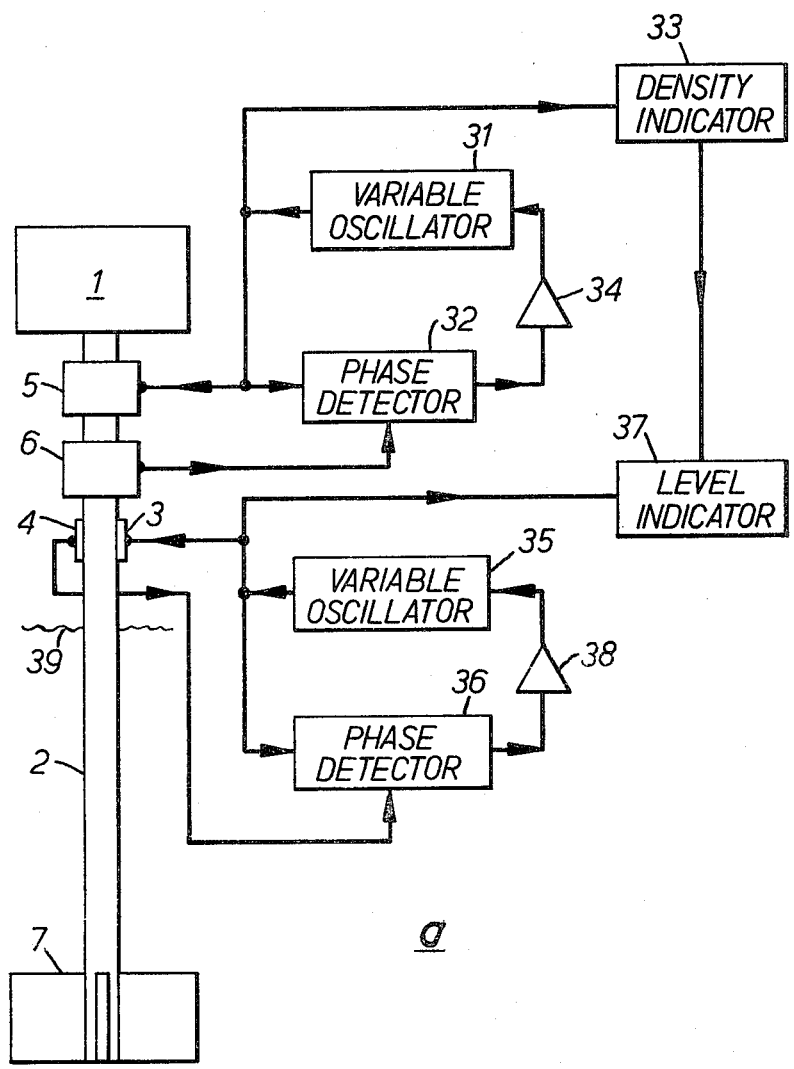
Figure 1:
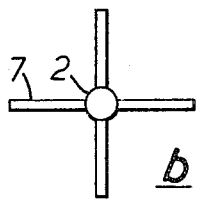

United States Patent [19]

Langdon

[11] 4,240,285
[45] Dec. 23, 1980

[54] MEASUREMENT OF THE DENSITY OF LIQUIDS

[75] Inventor: Roger M. Langdon, Colchester, England

[73] Assignee: The Marconi Company Limited, Chelmsford, England

[21] Appl. No.: 64,818

[22] Filed: Aug. 8, 1979

[30] Foreign Application Priority Data

Aug. 9, 1978 [GB] United Kingdom ............... 32803/78

[51] Int. Cl.³ ..................... G01N 9/00; G01F 23/28
[52] U.S. Cl. ................................. 73/32 A; 73/290 V
[58] Field of Search .................. 73/32, 32 A, 290 V, 73/291; 310/321, 323, 333

[56] References Cited

U.S. PATENT DOCUMENTS

| 2,354,923 | 8/1944 | McNamee | 73/32 A |
| 3,225,588 | 12/1965 | Moulin et al. | 73/32 A |
| 3,690,147 | 9/1972 | Kuenzler | 73/32 A |
| 4,129,031 | 12/1978 | Tehon et al. | 73/32 A |

*Primary Examiner*—James J. Gill
*Attorney, Agent, or Firm*—Diller, Ramik & Wight

[57] ABSTRACT

A device for measuring the density of a liquid relies on the generation of resonant modes in a torsional vibration set up in a paddle which is immersed in the liquid. The frequency at which a resonance mode, usually a fundamental, is produced is a function of the density of the liquid. A feedback circuit is described which varies the frequency of an oscillator producing the vibrations so as to enable the frequency at which the resonance mode exists to be automatically found. Transducers for generating and detecting the torsional vibration are located at one end of a rod above the surface of the liquid, and the paddle is mounted on the other end of the rod.

6 Claims, 3 Drawing Figures

MEASUREMENT OF THE DENSITY OF LIQUIDS

This invention relates to devices for measuring the density of liquids and seeks to provide such a device in which the measurement of density can be accomplished in a simple and reliable manner and in which the use of mechanically moving parts is avoided.

According to the present invention a device for measuring the density of a liquid includes a member arranged for immersion into the liquid, means for applying a torsional vibration to said member so as to move a portion of the liquid in which the member is immersed, and means for varying the frequency of the torsional vibration to produce a resonance mode, the frequency of the vibration at the resonance mode being indicative of the density of the liquid.

Preferably the means for determining the presence of a resonance mode includes a phase detector for comparing the phase of a torsional wave at the means for applying the torsional vibration with the phase of the wave at means for detecting the presence of a torsional vibration.

Preferably again the said member is in the form of a paddle. A plurality of paddle blades can be provided.

The transducers for applying the torsional vibration to the paddle and for sensing the resultant torsional vibration induced in the paddle can be attached to an elongate member, the transducers being mounted on the elongate member at points remote from said paddle.

Alternatively the transducers can be mounted on a body to which the elongate member is attached at its upper end, the transducers for applying the torsional vibration being mounted on spokes which radiate from a central hub which is coaxial with the longitudinal axis of the elongate member.

As the elongate member passes through resonant modes in dependence on the frequency of the torsional vibration induced in it, the phase at the sensor transducer undergoes a rapid change from a first to a second level, and the frequency of the torsional vibration can be controlled to maintain a phase difference between the transducers which apply the wave and which sense it, at a level intermediate between said first and second phase levels, so as to sustain a resonance mode. As the density of the liquid in which the paddle is immersed determines the frequency at which a resonance mode can be sustained, the density can be deduced.

The device for measuring the density of a liquid may be combined with a device for detecting the level of a liquid as is described in German printed application No. 2,839,634. Although for many purposes it is necessary to ascertain the density of a liquid directly, it is found that the operation of a device which measures the level of a liquid in accordance with the patent application referred to above is dependent on the density of the liquid itself.

Figure 2:
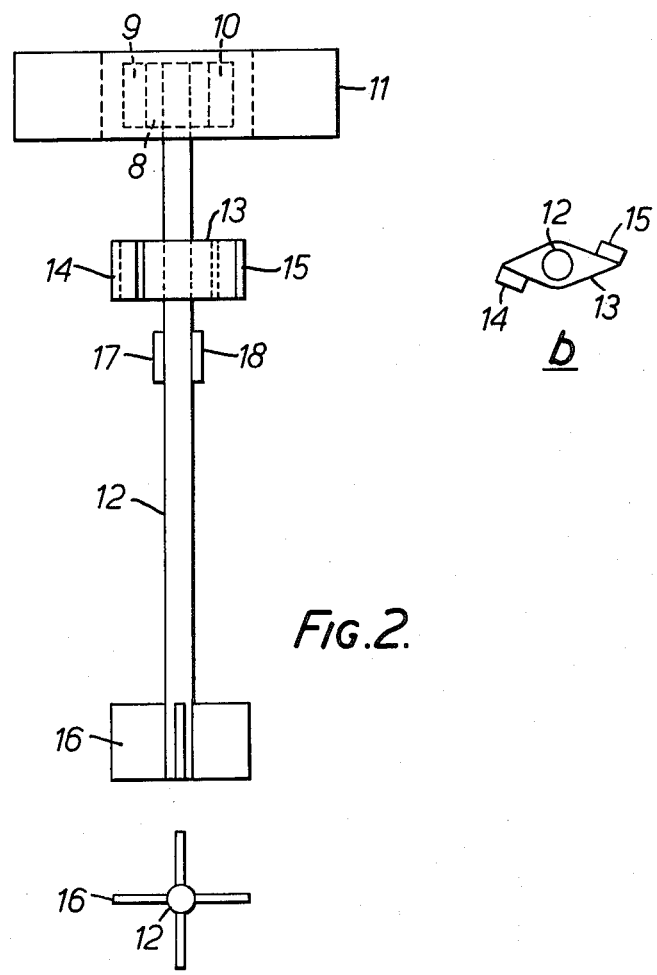
Figure 3:
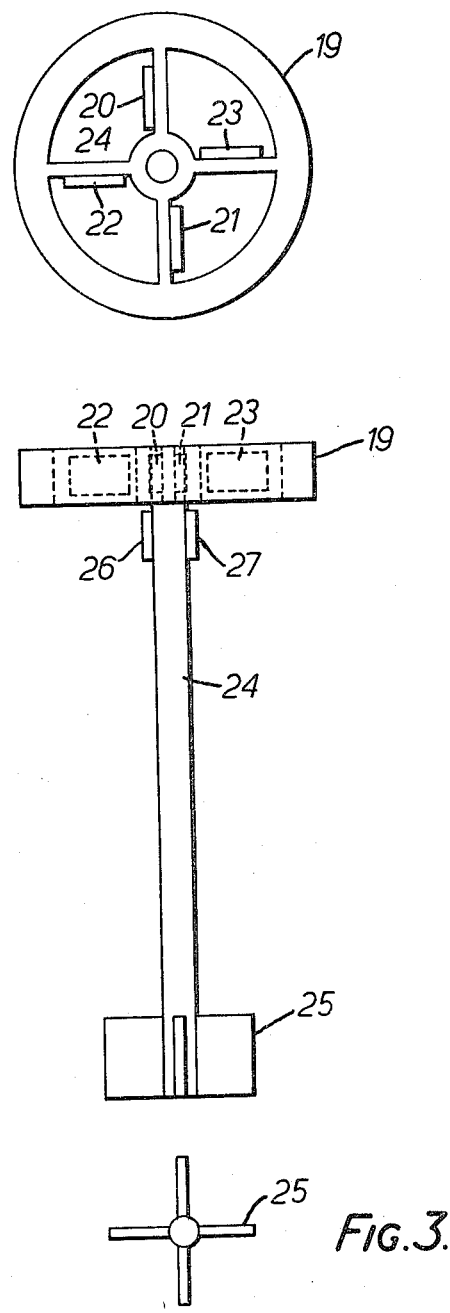

The present invention is further described by way of example with reference to the accompanying drawings in which, FIG. 1(a and b) illustrates diagrammatically a device for measuring the density of a liquid in accordance with the present invention and FIGS. 2 and 3 illustrate modifications thereof.

FIG. 1a illustrates a device which is capable of providing an indication of the density of a liquid and which is also able to provide an indication of the level of a liquid in which it is partially immersed. A round elongate rod 2, formed of glass is attached to a relatively massive body 1 which is sufficiently large so as not to move significantly in response to flexural or torsional movements induced in rod 1. A transducer 5 is mounted on the rod 2 and is such as to induce torsional vibrations in the rod. A transducer 6, which in practice is similar to transducer 5, is arranged to sense and detect the presence of these torsional vibrations. Further transducers 3 and 4 are mounted in contact with the rod 2 and are arranged to respectively generate and sense the presence of flexural waves in the rod 2. A four bladed glass paddle 7 is mounted on the lower end of the rod 2.

A variable oscillator 31 is coupled to the transducer 5 and to a density indicator 33 and also feeds a phase detector 32. The output of the transducer 6 is coupled to a second input of the phase detector 32. The output of the phase detector 32 is coupled via a high gain amplifier 34 to the input of the variable oscillator 31 so as to control its frequency of oscillation. By means of this feedback circuit arrangement the frequency of the variable oscillator 31 is adjusted so as to provide a torsional resonant mode in the rod 2 and the paddle 7. Generally the fundamental mode will be chosen.

A similar circuit is coupled to the transducers 3 and 4 so as to produce resonant flexure waves in the rod 2 and the paddle 7. In this case a variable oscillator 35 is arranged to feed the transducer 3 and also a phase detector 36. The other input of the phase detector is fed from the sensing transducer 4. The output of the phase detector 36 is coupled via a high gain amplifier 38 to the variable oscillator 35 so as to control its frequency of oscillation. The output of oscillator 35 and an output from density indicator 33 feed a level indicator 37.

The rotational axis of the paddle 7, which is illustrated in plan view in drawing b of FIG. 1 is arranged to coincide with the axis of the rod 2 and the paddle may be in the form of a wheel as shown having four paddle blades, although any number of blades may be provided as convenient. The transducers 3, 4, 5 and 6 may be of a piezo electric or electromagnetic type and the application of a sinusoidal voltage to the transducer 5 from the oscillator 31 produces a torsional vibration in rod 2 and the paddle 7 at the applied frequency. The sensor transducer 6, which is mounted on the rod 2 generates an output which is proportional to the torsional vibration amplitude of rod 2. It may generate an output voltage, which is proportional to the angular displacement, the angular velocity or the angular acceleration of rod 2 about its axis, dependent on the nature of the transducer. Application of a sinusoidal voltage of constant amplitude and variable frequency to the transducer 5 causes the rod 2 and the paddle 7 to resonate in a torsional mode at certain frequencies which are characteristic of the dimensions and materials of these components and in particular the resonant frequency is dependent on the moment of inertia of the paddle 7, which is partially dependent on the density of a liquid in which it is immersed. Typically the fundamental resonance mode is at a frequency of a few kilohertz.

Adjustment of the frequency of oscillation of the variable oscillator 21 to pass through a resonance frequency causes a large increase in torsional vibration amplitude, which produces a large increase in the output voltage provided by the transducer 6. The feedback circuit provided which includes the phase detector 32 sets the oscillator frequency at a value for which the output voltage from transducer 6 is a maximum. When this condition is satisfied the rod 2 and the paddle 7 oscillate at a resonance frequency. In operation, the device shown in FIG. 1 is mounted in a fixed position by means of a supporting structure (not shown) attached to the body 1 so that the paddle 7 is totally immersed in a liquid whose density is to be measured. In FIG. 1, the surface of this liquid is indicated by the line 39. The torsional resonance frequency is a function of the moment of inertia of the paddle 7 and the effective value of this is increased by the reactive force of the liquid acting on the blades of the paddle 7. As this reactive force is approximately proportional to the density of the liquid the resonance frequency varies inversely with changes in liquid density. Thus the density indicator 33 is arranged to measure the frequency applied to it and is calibrated using liquids of known density so that from a measurement of the frequency applied to it the density of the liquid can be indicated.

The measurement of density by means of the torsional vibration is unaffected by changes in the liquid level 39 provided that the paddle 7 is totally immersed in the liquid and provided that the level is not so high as to adversely affect the operation of the transducers 3, 4, 5 and 6.

In order to determine the level of the liquid surface 39, the variable oscillator 35 supplying the transducer 3 is varied in frequency, whilst its electrical amplitude is held constant. The rod 2 resonates in a flexure mode at certain specific frequencies and at resonance a large increase in flexure vibration amplitude occurs at resonance frequencies, thereby producing a large increase in the electrical output obtained from transducer 4. The feedback circuit shown in FIG. 1 is arranged to adjust the frequency of the variable oscillator 35 to a value which gives a maximum output from the transducers 4, i.e. a flexure resonance frequency of rod 2.

The resonance frequency of flexure vibration is dependent on the extent to which the rod 2 is immersed in the liquid, as is explained in our co-pending patent application number 38016/77. This effect stems from the change in the flexure wave velocity caused by the action of the liquid on the rod 2. If the device is held in a fixed position while the liquid level 39 is varied, the frequency will change by an amount which depends on the level of the liquid and the density of the liquid. By utilising the measurement of density obtained from the density indicator 33 a true indication of the liquid level can be determined by the level indicator 37.

A modified form of the device is shown in FIG. 2, but in which details of the control and feedback circuits have been omitted since they correspond to those shown in FIG. 1. In FIG. 2, a glass tube or rod 12 has a four-bladed glass paddle 16 attached at its lower end and the other upper end is bonded with an epoxy resin into a metal block 8. Piezo electric ceramic plates 9 and 10 are attached to a common surface of the block 8 as shown and the other surface of the plates 9 and 10 are attached to a flat surface formed inside a rectangular slot cut into a relatively massive circular metal block 11, as shown in FIG. 2a. The block 11 is made sufficiently large so that its moment of inertia about the axis of the tube or rod 12 is much larger than the moment of inertia of the vibrating part of the structure, which is constituted by the tube or rod 12 and the paddle 16. This enables the block 11 to be mounted on a supporting structure without significantly affecting the frequency of torsional vibration.

The piezo electric transducers 9 and 10 are polarised such that the application of a voltage between the blocks 8 and 11 causes transducer 9 to contract in thickness and transducer 10 to expand. This causes a rotation of the tube or rod 12 about its axis and the application of a sinusoidal voltage between blocks 8 and 11 causes a torsional vibration to be set up in the tube 12 and the paddle 16. In practice, this torsional vibration would originate from an oscillator such as oscillator 31 shown in FIG. 1. The amplitude of the torsional vibration is measured by piezo electric ceramic transducers 14 and 15 which are mounted on the end faces of a further metal block 13, which is mounted rigidly on the glass tube on rod 12. The shape of the block 13 is indicated in plan view in drawing 2b. The block 13 is attached to the tube on rod 12 by means of an epoxy resin and is located at approximately one quarter of the length of tube 12 from block 8. The transducers 14 and 15 have electrodes attached to their free surfaces, which are connected together and the transducers are polarised so that a voltage is produced on the electrodes in proportion to the angular acceleration of tube on rod 12. Thus transducers 14 and 15 give an output voltage which is proportional to the torsional vibration amplitude of tube 12. The output from transducers 14 and 15 is used in a similar manner to the output of transducers 6 shown in FIG. 1 so as to control the frequency of an oscillator so as to produce a torsional resonance frequency to the tube 12. Immersion of the paddle 16 in a liquid causes the torsional resonance frequency to change by an amount which is dependent on the liquid density.

So that the level of a liquid can be determined piezo electric ceramic transducers 17 and 18 are attached to the tube 12 in a manner similar to transducers 3 and 4 shown in FIG. 1.

A further alternative form of construction is shown in FIG. 3 in which a glass tube on rod 24 is attached to a glass bladed paddle 25 at its lower end and to the centre of an aluminium disc 19 at its upper end. The disc 19 is in the form of a four spoke wheel as shown and piezo electric ceramic transducers 20, 21, 22 and 23 are bonded to the flat surfaces of the spokes with an electrically conductive epoxy resin. The piezo electric transducers 20 and 21 perform the function of transducers 9 and 10 of FIG. 2 and the application of a voltage to the electrodes on the surfaces of each of these transducers causes it to bend and so produce a rotation of the tube 12 about its axis. Transducers 22 and 23 perform the function of transducers 14 and 15 in FIG. 2.

I claim:

1. A device for measuring the density of a liquid including a member arranged for immersion into the liquid, first transducer means for applying a torsional vibration to said member so as to move a portion of the liquid in which the member is immersed, and means for varying the frequency of the torsional vibration to produce a resonance mode, the frequency of the vibration at the resonance mode being indicative of the density of the liquid, and wherein said first transducer means for applying the torsional vibration to the member and second transducer means for sensing the resultant torsional vibration induced in the member are coupled to an elongate member arranged to be partially immersed in the liquid, one end of the elongated member being attached to a relatively massive body located above the surface of the liquid, the first and second transducer means also being mounted above the surface of the liquid at points adjacent to the relatively massive body, and the member being mounted at a generally free end portion of the elongated member which is remote from said first and second transducer means and thereby adapting said member for suspended immersion in the associated liquid.

2. A device as claimed in claim 1 including means for determining the presence of a resonance mode which includes a phase detector for comparing the phase of a torsional wave at the first transducer means with the phase of the wave at the second transducer means.

3. A device as claimed in claim 1 and wherein the said member is in the form of a paddle.

4. A device as claimed in claim 1 and wherein the first and second transducer means are attached to the elongate member, the first and second transducer means being mounted on the elongate member at points remote from said paddle.

5. A device as claimed in claim 1, and wherein the first and second transducer means are mounted on a body to which the elongate member is attached at its upper end, the first transducer means being mounted on spokes which radiate from a central hub which is coaxial with the longitudinal axis of the elongate member.

6. A device as claimed in claim 1 and including means for applying a flexural vibration to said elongate member so as to move a portion of the liquid in which the member is immersed, means for varying the frequency of the flexural vibration to produce a resonance mode, the frequency of the vibration at the resonance mode being indicative of the level of the surface of the liquid for a liquid of given density, and means for utilising the value of the frequency of the torsional vibration at the resonance mode to produce a corrected indication of the position of the liquid surface.

* * * * *